US010016565B2

(12) United States Patent
Nielsen et al.

(10) Patent No.: US 10,016,565 B2
(45) Date of Patent: *Jul. 10, 2018

(54) MEDICAL ASSEMBLY WITH MONITORING DEVICE

(71) Applicant: Novo Nordisk A/S, Bagsvaerd (DK)

(72) Inventors: Ole Christian Nielsen, Hilleroed (DK); John Oestergaard Madsen, Roedovre (DK)

(73) Assignee: Novo Nordisk A/S, Bagsvaerd (DK)

( * ) Notice: Subject to any disclaimer, the term of this patent is extended or adjusted under 35 U.S.C. 154(b) by 365 days.

This patent is subject to a terminal disclaimer.

(21) Appl. No.: 14/741,988

(22) Filed: Jun. 17, 2015

(65) Prior Publication Data
US 2015/0273163 A1  Oct. 1, 2015

Related U.S. Application Data

(63) Continuation of application No. 13/121,010, filed as application No. PCT/EP2009/062782 on Oct. 1, 2009, now Pat. No. 9,089,650.
(Continued)

(30) Foreign Application Priority Data

Oct. 1, 2008 (EP) ..................... 08165638
Oct. 6, 2008 (EP) ..................... 08165935

(51) Int. Cl.
A61M 5/31 (2006.01)
A61M 5/50 (2006.01)
(Continued)

(52) U.S. Cl.
CPC .......... A61M 5/5086 (2013.01); A61M 5/178 (2013.01); A61M 5/31525 (2013.01);
(Continued)

(58) Field of Classification Search
CPC .......... C07K 14/43595; Y10S 435/968; Y10T 436/2525; A61M 2205/3306;
(Continued)

(56) References Cited

U.S. PATENT DOCUMENTS 5,628,309 A    5/1997   Brown
6,302,855 B1  10/2001   Lav et al.
(Continued)

FOREIGN PATENT DOCUMENTS

CN       1414869 A      4/2003
JP    2005-287676 A    10/2005
(Continued)

Primary Examiner — Imani Hayman
(74) Attorney, Agent, or Firm — Wesley Nicholas

(57) ABSTRACT

An assembly including a drug delivery device and a monitoring device adapted to detect an action taking place in the drug delivery device. The drug delivery device including a main portion having a drug expelling mechanism for expelling drug from the reservoir through an outlet, a housing in which at least a portion of the expelling mechanism is arranged, and a member able to attach a cover to the drug delivery device. The cover is adapted to cover the outlet when mounted. The monitoring device includes a housing portion, a member for detecting an action taking place in the drug delivery device, and at least one member adapted to engage a member present on the main portion. By this arrangement the monitoring device can be placed in a pre-determined position relative to the main portion, allowing efficient transmission of information between the monitoring device and the main portion.

15 Claims, 10 Drawing Sheets

Related U.S. Application Data

(60) Provisional application No. 61/102,510, filed on Oct. 3, 2008.

(51) Int. Cl.
    *A61M 5/315*     (2006.01)
    *G06F 19/00*     (2018.01)
    *A61M 5/178*     (2006.01)
    *A61M 5/24*     (2006.01)
    *A61M 5/32*     (2006.01)

(52) U.S. Cl.
CPC .... *A61M 5/31533* (2013.01); *A61M 5/31535* (2013.01); *G06F 19/3468* (2013.01); *A61M 5/24* (2013.01); *A61M 5/31548* (2013.01); *A61M 5/3202* (2013.01); *A61M 2205/3306* (2013.01); *A61M 2205/3317* (2013.01); *A61M 2205/3375* (2013.01); *A61M 2205/3553* (2013.01); *A61M 2205/3561* (2013.01); *A61M 2205/3569* (2013.01); *A61M 2205/3576* (2013.01); *A61M 2205/3584* (2013.01); *A61M 2205/3592* (2013.01); *A61M 2205/52* (2013.01); *A61M 2205/581* (2013.01); *A61M 2205/8206* (2013.01); *A61M 2205/8212* (2013.01); *A61M 2205/8243* (2013.01); *A61M 2207/00* (2013.01)

(58) Field of Classification Search
CPC .. A61M 2205/3317; A61M 2205/3375; A61M 2205/3553; A61M 2205/3561; A61M 2205/3569; A61M 2205/3576; A61M 2205/3584; A61M 2205/3592; A61M 2205/52; A61M 2205/581; A61M 2205/8206; A61M 2205/8212; A61M 2205/8243; A61M 2207/00; A61M 5/178; A61M 5/24; A61M 5/31525; A61M 5/31533; A61M 5/31535; A61M 5/31548; A61M 5/3202; A61M 5/5086; G06F 19/3468

See application file for complete search history.

(56) References Cited

U.S. PATENT DOCUMENTS

| | | |
|---|---|---|
| 6,482,185 B1 | 11/2002 | Hartmann |
| 6,589,229 B1 | 7/2003 | Connelly et al. |
| 6,652,489 B2 | 11/2003 | Trocki et al. |
| 6,817,986 B2 | 11/2004 | Slate et al. |
| 7,540,856 B2 | 6/2009 | Hitchins et al. |
| 8,721,596 B2 | 5/2014 | Trocki et al. |
| 2004/0133183 A1 | 7/2004 | Trocki et al. |
| 2006/0167419 A1 | 7/2006 | Fiechter et al. |
| 2008/0195052 A1 | 8/2008 | Hjertman et al. |

FOREIGN PATENT DOCUMENTS

| | | |
|---|---|---|
| WO | 9902210 A1 | 1/1999 |
| WO | 03/005891 | 1/2003 |
| WO | 2006045525 | 5/2006 |
| WO | 2007/107564 A1 | 9/2007 |

MEDICAL ASSEMBLY WITH MONITORING DEVICE

CROSS-REFERENCE TO RELATED APPLICATIONS

This application is a continuation of U.S. application Ser. No. 13/121,010, filed Jul. 22, 2011 (Notice of Allowance mailed), which is a 35 U.S.C. § 371 national stage application of International Patent Application PCT/EP2009/062782 (published as WO2010/037828), filed Oct. 1, 2009, which claimed priority of European Patent Application EP 08165638.1 and EP 08165935.1, filed Oct. 1, 2008 and Oct. 6, 2008, respectively; this application further claims priority under 35 U.S.C. § 119 of U.S. Provisional Application 61/102,510, filed Oct. 3, 2008; the contents of which are incorporated herein by reference.

The present invention generally relates to medical devices for which the generation, collecting and distribution of data are relevant. In specific embodiments the invention relates to medical delivery devices in combination with means which provide ease of use in a cost-effective way.

BACKGROUND OF THE INVENTION

In the disclosure of the present invention reference is mostly made to the treatment of diabetes by delivery of insulin, however, this is only an exemplary use of the present invention.

For users of medication delivery devices it may be a cumbersome process to keep track of the amount of doses being expelled from the medication delivery device. This process is being further complicated if the time of injection, date of injection etc. are also to be monitored. Addressing this problem a number of solutions have been proposed which would help a user to generate, collect and distribute data indicative of the use of a given medical device.

For example, WO 2007/107564 describes an electronic "add-on" module adapted to be attached to and measure signals generated by a mechanical pen device. The detected signals may be used to detect different events, e.g. different sounds indicating setting a dose respectively ejecting a dose. A memory stores detected doses together with a time stamp, e.g. for several months. The module is provided with wireless means for transmitting detected data to an external unit, e.g. computer or another portable device (e.g. cell phone, PDA) for further processing and visualization. Further external devices for a pen device are shown in U.S. Pat. No. 6,482,185, and WO 03/005891. WO 99/02210 discloses a durable cap for attachment to a mechanical pen device. When the cap is mounted it can be rotated relative to the pen housing and thereby used to set a dose which is then registered in the cap by means of an electronic transducer.

As an alternative to the add-on solution, WO 2006/04552 describes an electronic module adapted to be integrated into a drug delivery device, e.g. a disposable pen device. The module is adapted to record information indicative of a pen dosing parameter, and subsequently transmit data (e.g. time, dose, type of insulin) to an external device for analysis and display. The external device may be in the form of a cap attachable to the pen, the cap providing communication means allowing the cap to transmit data to a further external device, e.g. computer. The cap may be provided with a display showing e.g. time and dose data.

Having regard to the above, it is an object of the present invention to provide devices and methods allowing secure, easy and cost-effective operation of components, devices and systems for the generation, collecting and distribution of data associated with the use of a medical device, especially a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect an assembly is provided comprising an assembly comprising a drug delivery device having or being adapted to receive a reservoir for a drug, an outlet for the drug, a drug expelling mechanism for expelling drug from the reservoir and out through the outlet, a housing in which at least a portion of the drug expelling mechanism is arranged, and first coupling means for a cap. The assembly further comprises a cap adapted to cover the outlet, the cap comprising second coupling means for engaging the first coupling means, as well as a monitoring device comprising a housing portion, means for detecting and/or registering an action performed in the drug delivery device, and third coupling means adapted to engage the first coupling means on the drug delivery device. By this arrangement the monitoring device can be arranged in a pre-determined mounted position relative to the drug delivery device when the first and third coupling means engage each other, this allowing information to be transferred between the drug delivery device and the monitoring device. Further, in the mounted position the monitoring device does not cover the outlet when arranged in the mounted position, thus allowing an amount of drug to be expelled from the reservoir while the monitoring device is coupled to the drug delivery device.

Transfer of information from a housing portion of the drug delivery device may be by non-galvanic means, e.g. audible, optical, vibration or electromagnetic. The monitoring device may be placed in a pre-determined and non-rotational position relative to the housing when the first and third coupling means engage each other, this allowing information to be transferred between the drug delivery device and the monitoring device (e.g. by non-galvanic means) in the most optimal way. Alternatively the transfer of information may be by galvanic means, e.g. contacts made from conducting plastic. Instead of being provided with a reservoir, the assembly may also be adapted to receive a reservoir with an outlet, the cap being adapted to cover the outlet when such a reservoir is arranged in the main portion.

The monitoring device may comprise fourth coupling means adapted to engage the second coupling means, this allowing the cover portion, e.g. cap to be attached to the main portion via the monitoring device. Alternatively the monitoring device may comprise a fourth coupling means adapted to engage fifth coupling means arranged on a second cover portion, e.g. cap, this allowing the second cover portion, e.g. cap to be attached to the main portion via the monitoring device.

The monitoring device may comprise means for biasing a portion of the monitoring device against a housing portion of the drug delivery to thereby enhance the non-galvanic transfer of information between the two devices, e.g. vibrations.

In an exemplary embodiment the monitoring device comprises a mounting portion and a monitoring portion, the mounting portion comprising the third coupling means, wherein the mounting portion and the monitoring portion comprise releasable coupling means for coupling the two portions. The mounting portion may comprise non-releasable coupling means, e.g. adhesive, for engaging the drug delivery device.

To further secure and position the monitoring device it may be provided with a further coupling means adapted to engage a specific coupling structure on the drug delivery device, e.g. an opening for dose dial.

The drug expelling mechanism may be mechanical or substantially mechanical, i.e., it can include some electronic components, and the detection means may be adapted to detect audible, vibrational (e.g. "click" sounds), optical or electromagnetic signals generated by the drug expelling mechanism. The detection means can include ultrasound detection, and/or accelerometer detection. The drug expelling mechanism may be adapted to set and expel a set dose, with the detection means being adapted to detect the size of a dose being set and/or the size of a dose being expelled. The monitoring device may comprise means for transferring data to an external device, e.g. by wireless IR or RF means.

In an embodiment an assembly is provided comprising a medical device and a monitoring device adapted to detect an action taking place in the medical device, wherein information is transferred through a housing portion of the medical device by non-galvanic means. The medical device comprises a mechanism adapted to perform an action, a housing in which at least a portion of the mechanism is arranged, and first coupling means. The monitoring device comprises a housing portion, means for detecting an action performed by the mechanism, and second coupling means adapted to engage the first coupling means. By this arrangement the monitoring device can be placed in a pre-determined position relative to the medical device when the first and second coupling means engage each other, this allowing information to be transferred between the medical device and the monitoring device by non-galvanic means. This embodiment may be modified as described above.

In a further embodiment an assembly is provided comprising a medical device and a monitoring device adapted to detect and/or register an action taking place in the medical device. The medical device comprises a mechanism adapted to perform an action, a housing portion in which at least a portion of the mechanism is arranged, first coupling means arranged on the housing, and a cover portion, e.g. cap adapted to be mounted on the housing portion, the cover portion, e.g. cap comprising second coupling means for engaging the first coupling means on the housing portion. The monitoring device comprises a housing portion, means for detecting and/or registering an action performed by the mechanism, and third coupling means adapted to engage the first coupling means, whereby the monitoring device can be arranged in a pre-determined position relative to the housing portion when the first and third coupling means engage each other, this allowing information to be transferred between the medical device and the monitoring device. Information may be transferred through a housing portion of the drug delivery device by non-galvanic means. This embodiment may also be modified as described above.

In a further embodiment an assembly is provided comprising a medical device and a monitoring device adapted to detect and/or register a state of (e.g. an amount of a contained drug) or an action performed in the medical device (e.g. by a mechanism arranged at least partly in a housing of the medical device). The medical device comprises a housing, first coupling means associated with the housing, and a cover portion, e.g. cap adapted to be mounted on the housing, the cover portion, e.g. cap comprising second coupling means for engaging the first coupling means. The monitoring device comprises a housing, means for detecting and/or registering a state of or an action performed in the medical device, and third coupling means adapted to engage the first coupling means, whereby the monitoring device can be arranged in a pre-determined position relative to the housing portion when the first and third coupling means engage each other, this allowing information to be transferred between the medical device and the monitoring device. Information may be transferred through a housing portion of the drug delivery device by non-galvanic means. This embodiment may also be modified as described above.

In the above-described embodiments the monitoring device may be arranged to not cover the outlet when arranged in the mounted position, thus allowing an amount of drug to be expelled from the reservoir while the monitoring device is coupled to the drug delivery device. This embodiment may also be modified as described above.

In a yet further embodiment an assembly is provided comprising a medical device and a monitoring device adapted to detect and/or register a state of (e.g. an amount of a contained drug) or an action performed in the medical device (e.g. by a mechanism arranged at least partly in a housing of the medical device). The medical device comprises a housing and first coupling means. The monitoring device comprises a housing portion, means for detecting a state of or an action performed in the medical device, and second coupling means adapted to engage the first coupling means, thereby placing the monitoring device in a pre-determined position relative to the medical device when the first and second coupling means engage each other, this allowing information to be transferred between the medical device and the monitoring device. This embodiment may also be modified as described above.

In a specific embodiment, an assembly is provided which includes (a) a drug delivery device which can include a reservoir for a drug, an outlet for the drug, a drug expelling mechanism for expelling drug from the reservoir and out through the outlet, and a housing in which at least a portion of the drug expelling mechanism is arranged, (b) a mounting device which can include a non-releasable first coupling means for engaging the drug delivery device, and second coupling means, and (c) a monitoring device which can include a housing portion, means for detecting and/or registering an action performed in the drug delivery device, and releasable third coupling means for engaging the second coupling means of the mounting device. By this arrangement the mounting device can be arranged in a pre-determined mounted position relative to the drug delivery device when the second and third coupling means engage each other, this allowing information to be transferred between the drug delivery device and the monitoring device when the monitoring device is coupled with the mounting device. Further, the mounting and monitoring devices are adapted not to cover the outlet when arranged in the mounted positions, thus allowing an amount of drug to be expelled from the reservoir while the mounting device is coupled to the drug delivery device.

In a further specific embodiment, an assembly is provided comprising (a) a drug delivery device comprising a reservoir for a drug, the reservoir comprising a transparent area allowing a user to inspect at least a portion of the reservoir, an outlet for the drug, a drug expelling mechanism for expelling drug from the reservoir and out through the outlet, a housing in which at least a portion of the drug expelling mechanism is arranged, and a first coupling means for a cap, (b) a mounting portion comprising non-releasable coupling means for engaging the drug delivery device, and a third coupling means, and (c) a monitoring portion comprising a housing portion, means for detecting and/or registering an action performed in the drug delivery device, and a releasable coupling means for coupling the third coupling means of the mounting portion, whereby the mounting portion can be arranged in a pre-determined mounted position relative to the drug delivery device when the first and third coupling means engage each other, this allowing information to be transferred between the drug delivery device and the monitoring portion when the monitoring portion is coupled with the mounting portion, and whereby the mounting portion or monitoring portion do not cover the outlet when arranged in the mounted positions, thus allowing an amount of drug to be expelled from the reservoir while the mounting portion is coupled to the drug delivery device.

In a yet further specific embodiment, an assembly is provided including (a) a drug delivery device which can include a reservoir for a drug, an outlet for the drug, a drug expelling mechanism for expelling drug from the reservoir and out through the outlet, a housing in which at least a portion of the drug expelling mechanism is arranged, and a first coupling means for a cap, and (b) a monitoring device which can include a housing portion, means for detecting and/or registering an action performed in the drug delivery device, whereby the monitoring device and/or the drug delivery device has a conical or substantially conical shaped portion adapted to be axially and/or slidably attached to the drug delivery device such that when the monitoring device is mounted it is axially and rotational locked.

For all of the above embodiments, instead of being provided with a reservoir, the assembly may also be adapted to receive a reservoir with an outlet. When provided with a cap, the can be adapted to cover the outlet when such a reservoir is arranged in the drug delivery device.

It is contemplated that the monitoring device can be provided by itself, i.e., it need not be provided with an assembly including a drug delivery device and a cover portion or cap.

In a second aspect of the invention an assembly is provided comprising a drug delivery device and a cap device. The drug delivery device comprises a reservoir for a drug, an outlet for the drug, and a drug expelling mechanism for expelling drug from the reservoir and out through the outlet. The cap device is adapted to cover the outlet when mounted on the drug delivery device and comprises first contact means operatable between a first condition and a second condition, the first condition indicating that the cap device is in a fully mounted position on the drug delivery device, the second condition indicating that cap device has been moved a first distance away from the fully mounted position, second contact means operatable between a first condition and a second condition, the first condition indicating that the cap device is in a fully mounted position on the drug delivery device, the second condition indicating that cap device has been moved a second distance away from the fully mounted position, the second distance being longer than the first distance, and control means adapted to detect an event pattern for when the first and second contact means have been operated between their respective first and second condition. In this arrangement the control means is adapted to perform an action if a given event pattern is detected.

The second condition of the second contact means may be indicative of the cap being moved fully away from the drug delivery, and the second condition of the first contact means may be indicative of the cap being moved less than fully away from the drug delivery. In an exemplary embodiment the drug delivery device comprises an oblong portion defining an axial orientation and with the outlet being arranged at the distal end thereof, and the cap device comprises a generally oblong cavity adapted to receive the oblong portion of the drug delivery device thereby covering and protecting the outlet. In such an arrangement the second condition of the second contact means is indicative of the cap device being moved away from the drug delivery sufficiently to allow the cap device to be moved perpendicularly away from the drug delivery device, this being indicative of the cap having been fully removed from the drug delivery device.

The event pattern may correspond to the event that the second contact has been in its second condition in a predetermined amount of time, with the corresponding action performed by the control means being the creation of a time log representing the detected event as a function of time. The event pattern may also correspond to the event that the second contact has been in its first condition in a predetermined amount of time, and the first contact has been in its second condition in a predetermined amount of time, this being indicative of the cap not having been fully mounted on the drug delivery device, the corresponding action performed by the control means being the creation of a time log representing the detected event as a function of time.

The cap device may comprise means for transferring data to an external device, e.g. by wireless means, and the reservoir may be prefilled with a fluid drug.

In a specific embodiment an assembly is provided comprising (a) a drug delivery device having an oblong portion defining an axial orientation, and an outlet being arranged at the distal end of the oblong portion, and (b) a cap device adapted to cover the outlet when mounted on the drug delivery device, the cap device having (i) a generally oblong cavity adapted to receive the oblong portion of the drug delivery device thereby covering and protecting the outlet, (ii) contact means operatable between a first condition and a second condition, the second condition being indicative of the cap device being moved away from the drug delivery sufficiently to allow the cap device to be moved perpendicularly away from the drug delivery device, this being indicative of the cap having been fully removed from the drug delivery device, and (iii) control means adapted to detect the event pattern for when the contact means have been operated between the first and second condition, wherein the control means is adapted to perform an action if a given event pattern is detected.

In a further embodiment an assembly is provided comprising (a) a drug delivery device and (b) a cap device adapted to cover the outlet when mounted on the drug delivery device. The drug deliver device comprises a reservoir for a drug, an outlet for the drug, an oblong portion defining an axial orientation and with the outlet being arranged at the distal end thereof, a drug expelling mechanism for expelling drug from the reservoir and out through the outlet. The cap device comprises a generally oblong cavity adapted to receive the oblong portion of the drug delivery device thereby covering and protecting the outlet, and contact means operatable between a first condition and a second condition, the first condition indicating that the cap device is in a fully mounted position on the drug delivery device, the second condition indicating that the cap device has been moved away from the drug delivery device at least 50% (optionally 75 or 90%) of the way sufficient to allow the cap device to fully be moved perpendicularly away from the drug delivery device, this being indicative of the cap having been fully removed from the drug delivery device.

The 50% feature takes into account that it may be difficult to detect that the cap has been moved past a distally mounted relatively thin injection needle, however, the 50% will in most cases indicate that the cap is not merely loosely attached but has been moved fully away from the drug delivery device.

In a third aspect of the invention an assembly is provided comprising a drug delivery device and a cap device. The drug delivery device comprises a reservoir (e.g. prefilled) for a drug, an outlet for the drug, a drug expelling mechanism for expelling drug from the reservoir and out through the outlet, electronic circuitry, and a secondary power source for storing energy for driving the electronic circuitry. The cap device is adapted to cover the outlet when mounted on the drug delivery device and comprises a primary power source adapted to provide energy to the secondary means. In such an arrangement the drug delivery device and the cap device are provided with interacting transfer means adapted to transfer energy from the primary power source to the secondary power source when the cap device is mounted on the drug delivery device.

The cap device and the delivery device may comprise interacting coupling means for releasably mounting the cap device on the delivery device in a storing position, and wherein energy is transferred from the primary power source to the secondary power source when the cap device is mounted on the drug delivery device in its storing position. The energy may be transferred from the first energy means to the secondary energy means using a means from the group consisting of the members: galvanic contact and wireless transmission. The primary power source may be selected from the group consisting of the members: an electric battery, a rechargeable electric battery, a condensator, a user-operatable electric generator. The secondary power source may be selected from the group consisting of the members: a rechargeable electric battery, and a condensator.

In preferred embodiments the electronic circuitry may be adapted to perform one or more functions selected from the group consisting of the members: generating data representing the size of a dose set by the drug expelling mechanism, generating data representing the size of a dose expelled by the drug expelling mechanism, generating and storing a time log for data representing sizes of doses set by the drug expelling mechanism, generating and storing a time log for data representing sizes of doses expelled by the drug expelling mechanism, transmitting data to an external receiver, receiving data from an external transmitter, controlling a display adapted to display user-readable information, controlling indication means adapted to indicate when the secondary power source need to be recharged, and controlling control means adapted to prevent a dose to be set or expelled when the secondary power source need to be recharged.

In a fourth aspect of the invention a system is provided comprising at least first and second medical devices, each comprising electronic circuitry for generating and transmitting data, the system further comprising a data collecting device comprising electronic circuitry for receiving, storing and transmitting data. In such a system the medical devices are adapted to transmit data to the data collecting device, and the data collecting device is adapted to receive data from at least one medical device and transmit the received data to an external device or system. At least one of the medical devices may be a drug delivery device comprising a reservoir (e.g. prefilled) for a drug, an outlet for the drug, and a drug expelling mechanism for expelling drug from the reservoir and out through the outlet. At least one of the medical devices may be a BGM. In a specific embodiment, the data collecting device may be in the form of one of the medical devices.

In the above system the data collecting device may be in the form of one of the following devices: a BGM, a CGM, a drug delivery device, a mechanically controlled drug delivery device, an electronically controlled drug delivery device, a PDA, a mobile phone, a key ring device, a credit card sized device. At least one medical device may be in the form of one of the following devices: a BGM, a CGM, a drug delivery device, a mechanical drug delivery device, an electronically controlled drug delivery device. In the above system transmission of data between a medical device and the data collecting device may take place by wireless means, e.g. RF, IR, capacitive or inductive. Transmission of data may take place automatically when the data collecting device and a medical device are in the proximity of each other, e.g. within a given range.

In a specific embodiment a system is provided comprising (a) at least first and second drug delivery devices, each comprising a reservoir for a drug, an outlet for the drug, a drug expelling mechanism for expelling drug from the reservoir and out through the outlet, and electronic circuitry for generating and transmitting data, and (b) a data collecting device comprising electronic circuitry for receiving, storing and transmitting data. In such a system the drug delivery devices are adapted to transmit data to the data collecting device, and the data collecting device is adapted to receive data from at least one drug delivery device and transmit the received data to an external device or system.

As used herein, the term "drug" is meant to encompass any drug-containing flowable medicine capable of being passed through a delivery means such as a cannula or hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

Figure 1:
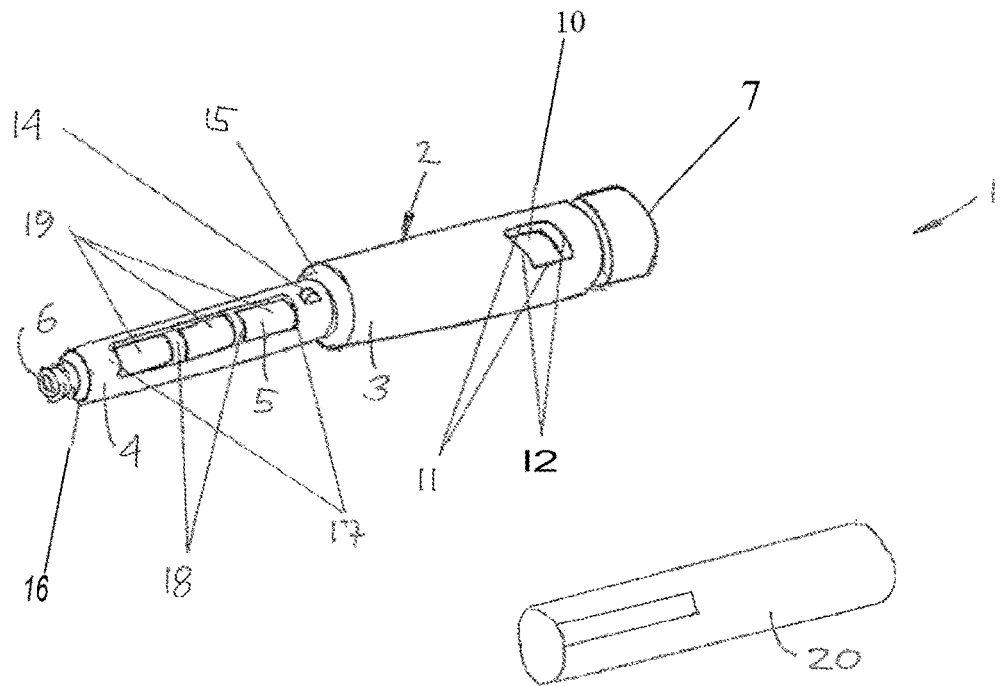
FIG. 1 shows a drug delivery pen.

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

The first aspect of the invention addresses the problems of enabling monitoring of patients behaviour regarding adherence to prescribed medical treatment by using an external accessory to a medical device, e.g. an insulin pen, enabling the accessory to monitor and e.g. log and e.g. even later communicate the use of the device to another device or/and to an inherent display. Where this can be a natural option for a durable device, e.g. a durable insulin pen, where this accessory or optional monitoring part can be mounted in very controlled environment during the manufactures management it is a much more difficult task for a patient to do in a properly and reliable manner. If the mounting should also be made on disposable medical devices, e.g. a number of successively used disposable pens, the task is further complicated because the accessory must be removed from one device in order to be mounted on another device. Besides the basically mechanically fixation challenges there will normally also be a certain area on the medical device which is the most preferred to use for a reliable monitoring of the use of the device, e.g. monitoring of the use of the device by vibrational, auditive, magnetic or/and other sensor means. For most sensors it is vital for the achievement of reliable data that the add-on monitoring device containing the sensor is placed very definitely.

An embodiment of the invention in accordance with the first aspect is in the following description referenced to a disposable insulin pen with the overall main shape of one or more cylinders in axial mechanical prolongation and with a number of holes and/or protrusions. The shape can also in detail be conically or oval or arc-shaped or other overall cylindrical shapes. The invention solves the two main problems in the mounting process of an accessory to a disposable device, namely (1) the correct fixation area and (2) the ability to demount and remount the durable accessory on a number of disposable devices in a cost beneficial way.

Firstly, in respect to the correct fixation area on the medical device this can be described as a correct axial and often further rotational placement on the medical device (e.g. an insulin pen). Most disposable medical devices in the type of disposable insulin pens have for one thing a thickest part (cylinder a like) and for another thing one or more thinner parts (cylinder a like) in mechanical prolongation with one another in an axial manner. This/these thickness transition(s) including end transition(s) can be used as mechanical reference(s) in the axial direction of the correct placement of an accessory to an insulin pen. Moreover insulin pens often have non-symmetrical (rotational) protrusions (e.g. in the form of reference taps for correct assembly of the pen or e.g. cap lock(s)) and/or holes (e.g. in the form of display windows) which can further be utilized for the correct partly axial placement but in particular the correct rotational placement by having a counterpart on the accessory part. A special case of the last mentioned reference point(s) above are non-mechanical unevenness, e.g. optical marks or field based marks (e.g. magnetic marks) for which the accessory part can be aligned rotationally by the user.

Secondly, the correct fixation of the accessory is about the often necessary tight coupling of the accessory to the insulin pen surface and the important ability to mount and demount the accessory in order to be used on another insulin pen. This part of the invention can be divided into two different attractive solutions depending on the shape of the insulin pen. One group includes a cheap second disposable part which is not reused but disposed together with the disposable pen after use the other group is about stand alone accessory solutions.

In a stand-alone solution the close but releasable coupling between the accessory and the medical device is achieved by an accessory that can be manually locked and unlocked and which in the locked position encircle more than half (more than 180 degrees) of the rotational perimeter by one or more interlocking parts. In the locked position a predominantly resulting perpendicular (to the axial direction of the insulin pen) spring function secures the necessary force to achieve a reliable close (tight) sensorial function of the accessory inherent sensor(s). Alternatively, the close coupling is achieved by utilizing a conically shape of the insulin pen and a corresponding conically shape of the accessory whereby the accessory can be squeezed to a close coupling (for the inherent sensor to work reliable). The locking of the axial position is achieved by a locking mechanism utilizing one or more protrusions and/or holes in the insulin pen combined with a compressibility of one or more parts of the accessory.

Alternatively, an additional disposable mounting part (or aid) is provided and the above-described accessory is modified in the manner, that it is not the accessory part itself which is mounted to the medical device but the disposable mounting part, hereby avoiding potential problems with the demounting of conical parts. The mounting part must then have means for transferring the sensorial signal to the mounted accessory and having either a counterpart for a locking/unlocking mechanism on the accessory part or a locking/unlocking mechanism for the accessory. Another way to mount a disposable mounting part for the accessory is to use adhesive, e.g. exposing the adhesive by removing a protective layer and placing it by either mechanically and/or field based guides and/or marks (including visual marks).

Referring to FIG. 1 a pen-formed drug delivery device 1 will be described. The pen comprises a main portion 2 having a proximal part 3 in which a drug expelling mechanism is arranged, and a distal reservoir part 4 in which a drug-filled cartridge 5 with an outlet 6 is arranged. A proximal-most button 7 serves to manually set and expel a desired dose of drug. This type of a pen-formed drug delivery device is well known, see e.g. WO 99/38554 to which reference is made for further details in respect of the internal construction of the shown pen. FIG. 1 further shows a number of thickness transitions, holes and protrusions which can be utilized for axial and rotational alignment and fixation of an accessory part. More specifically, the pen comprises an opening 10 for a dose dial, the opening being surrounded by edges 11, 12. Diameter transitions 15, 16 are provided between the proximal and distal part, respectively the distal part and the outlet. The distal reservoir part comprises a cartridge holder with a longitudinal opening 17 allowing the user to inspect the drug cartridge arranged in the holder, the opening having a number of cross-members 18 forming a number of windows 19. The cartridge holder may be releasable or non-releasable attached to the main portion depending on whether the device is pre-filled or adapted to receive a separate cartridge. The distal part comprises proximally a coupling detent 14 adapted to engage a corresponding coupling structure on the interior wall of a cap member 20 which in its mounted position is adapted to cover the reservoir portion and thus the outlet.

Figure 2:
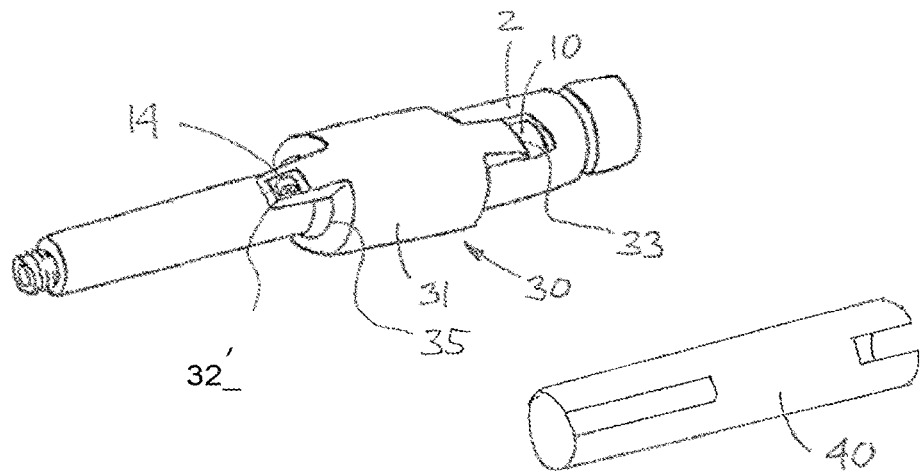
FIG. 2 shows a drug delivery pen with a monitoring device mounted.

FIG. 2 shows a monitoring device 30 mounted on the pen. The monitoring device may be of the type disclosed in WO 2006/04552 and comprises a housing portion 31, internal means for detecting an action taking place in the drug delivery device, and coupling means adapted to engage corresponding coupling means on the pen. In the shown embodiment the monitoring device comprises a third coupling portion 32, which is adapted to engage the detent 14, and a further coupling means 33, which is adapted to engage an edge of the opening 10. The monitoring device further comprises a distal edge 35 adapted to engage the transition 15 on the pen. By this arrangement the monitoring device can be placed in a pre-determined position both axially and rotational relative to the pen when corresponding coupling means engage each other, this allowing information to be transferred between the monitoring device and the main portion by e.g. non-galvanic means in the most optimal way. A further cap 40 is provided which is specifically adapted to be mounted on the pen when the monitoring device is mounted. Alternatively, the monitoring device may be designed with a configuration and coupling means which would allow the standard cap 20 to be mounted when using the monitoring device.

Figure 3:
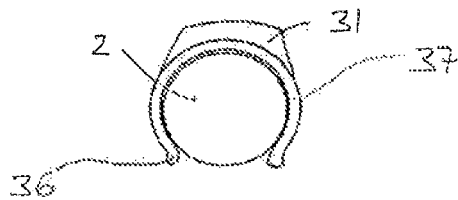
FIGS. 3 and 4 show means for biasing the monitoring device into contact with the pen.
Figure 4:
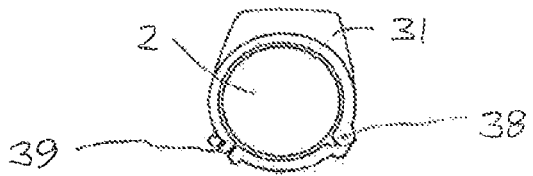

To ensure proper contact between a contact portion of the monitoring device and the corresponding predetermined exterior surface portion of the pen biasing means may be provided for forcing the two surfaces into contact with each other. This may be relevant if the monitoring device is adapted to detect actions by means of e.g. sound or vibrations. Correspondingly, FIG. 3 shows a clamp solution with flexible legs 36, 37, whereby the accessory can be clamped to the insulin pen and aligned by using thickness transitions and rotational guided by e.g. a protrusion on the pen. FIG. 4 shows an alternative in which the monitoring device comprises a pivoting locking member 38 with a releasable lock 39 whereby the accessory can be attached and locked to the insulin pen. Alternative the monitoring device and/or the pen could have a taper allowing the two portions to be arranged in a friction fit, e.g. a ring-formed monitoring device mounted on a pen housing having a longitudinal taper.

Figure 5:
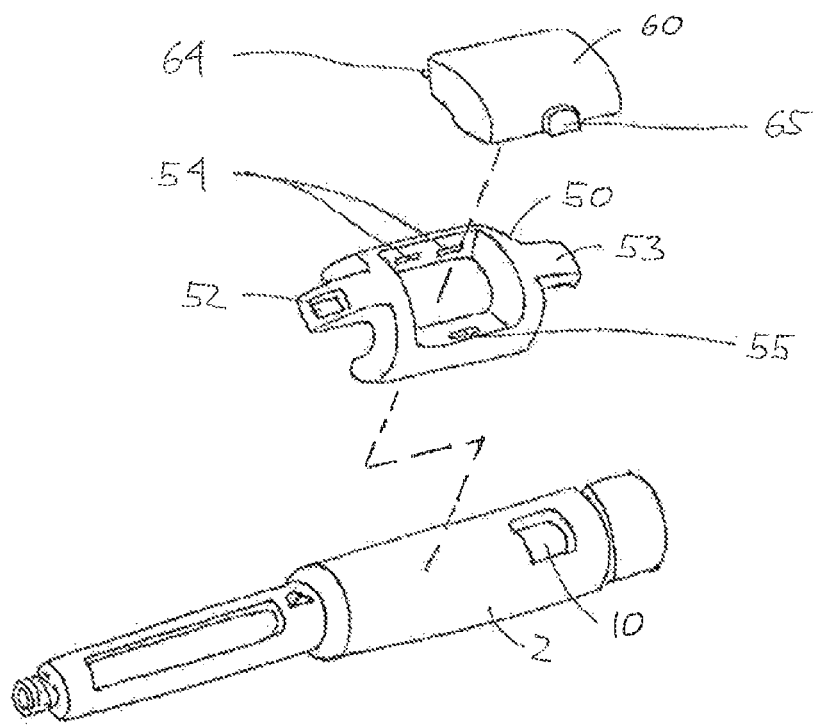
FIGS. 5 and 6 show a monitoring device comprising a mounting portion.
Figure 6:
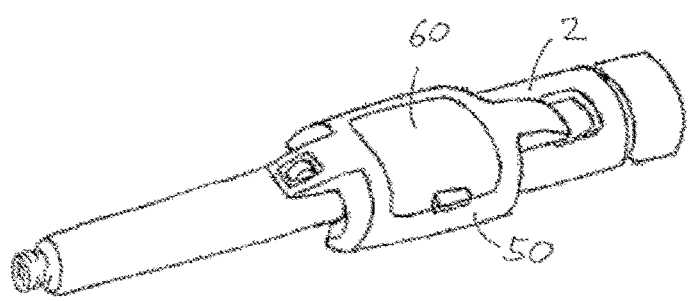
Figure 7:
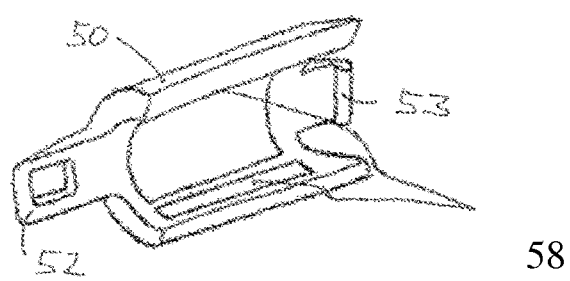
FIG. 7 shows the mounting portion.

FIG. 5 shows an embodiment where the monitoring device comprises a mounting portion (or accessory holder) 50 with an opening for receiving a monitoring portion (or accessory) 60. The mounting portion comprising coupling means 52, 53 as in the FIG. 3 or 4 embodiments, however, the mounting portion and the monitoring portion comprise further releasable coupling means 54, 55, 64, 65 for coupling the two portions together. The mounting portion may be provided with non-releasable coupling means for engaging the drug delivery device, e.g. adhesive portions 58 as shown in FIG. 7. On each adhesive area a cover paper is removed before attachment to the pen. Similarly, adhesive portions 58 can be substituted with a non-releasable locking mechanism (now shown). Alternatively the mounting portion can be provided with a "conical fit" ensuring good contact and a tight fit between the mounting portion and the drug delivery device. The accessory holder can still use guide and alignment features as described above. The accessory holder is meant to be disposed together with a disposable drug delivery pen after final use (e.g. insulin pen empty) and the accessory to be attached into a new accessory holder attached on a new disposable pen.

Figure 22:
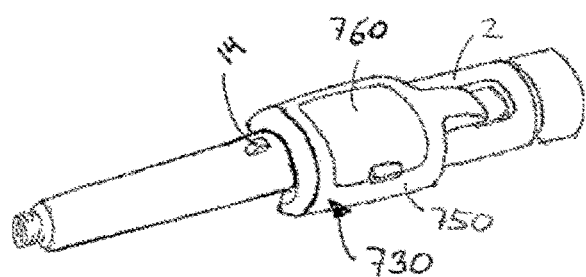
FIG. 22 shows an embodiment of a monitoring device mounted on a drug delivery device.

FIG. 22 shows an embodiment where the coupling means 14 intended for the original cap or cover of the medical device need not be occupied by the coupling means of the mounting portion (or accessory holder) 750 of a monitoring device 730 when mounted. Thus, the mounting portion (or accessory holder) 750 of the monitoring device does not cover the outlet when arranged in the mounted position, this allowing the original cover portion or cap to be mounted, or an amount of drug to be expelled from the reservoir while the monitoring device is coupled to the drug delivery device. Further, in the embodiment shown in FIG. 22, the monitoring portion 760 does also not cover the main portion or reservoir.

Figure 23:
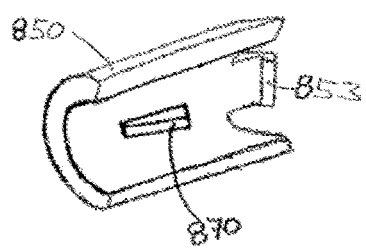
FIG. 23 shows a mounting portion.
Figure 24:
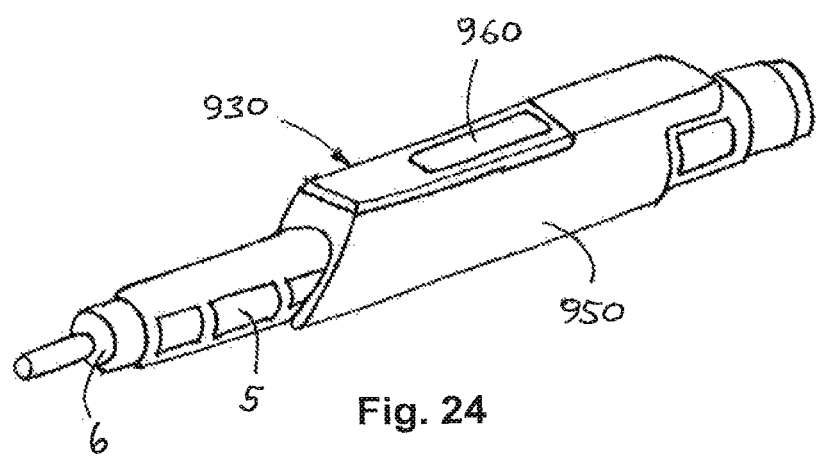
FIG. 24 shows a further embodiment of a monitoring device mounted on a drug delivery device.

FIG. 23 shows an embodiment where the interior of the mounting portion (or accessory holder) 850 in addition to coupling means 853 is provided with a coupling means 870 and the exterior of the medical device (not shown) can be complimentary shaped. For example, FIG. 24 shows an interior of a mounting portion is substantially conically shaped, and can engages the medical delivery device by way of a "conical fit" ensuring good contact between the mounting portion and the medical delivery device. The medical delivery device can further be provided with a coupling means which engages a complimentary coupling means 870 provided on the mounting portion to restrict and/or prevent rotational movement of the mounting means relative to the medical delivery device.

It is further contemplated that the mounting portion 850 described above can have a conical or substantially conical shaped portion, wherein a monitoring portion 860 can be coupled to the mounting portion. This is depicted in FIG. 24 which provides a monitoring device 930 comprising a mounting portion 950 and monitoring portion 960, the mounting portion having a conical or substantially conical shaped portion. A substantially conical and/or substantially circumferential portion of the mounting portion or monitoring device is contemplated where the substantially conical and/or substantially circumferential portion is able to expand to provide a tight fit when axially and slidably placed on the drug delivery device. Such a fit can be either releasable or non-releasable. For example, if a mounting portion is desired together with a separate monitoring portion, the mounting portion can be non-releasable from the drug delivery device, and the monitoring portion can be releasable from the mounting portion.

Figure 25:
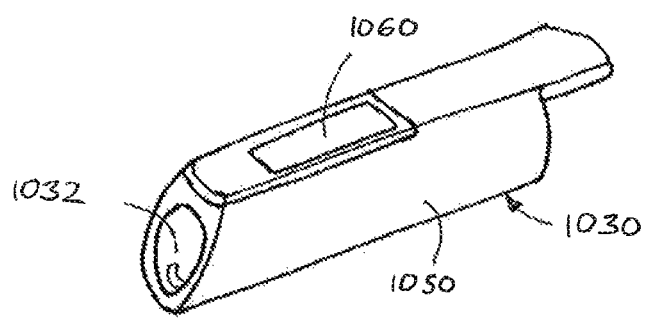
FIG. 25 shows a further embodiment of a monitoring device.

Alternatively, FIG. 25 shows a unitary monitoring device 1030 in which the monitoring portion 1060 is formed integrally with the mounting portion 1050 provided with coupling means 1032 for releasably engage corresponding coupling means on a drug delivery device, e.g. similar to the coupling means 14 shown in FIG. 1. Such a configuration can provide an economical and efficient means for connecting add-on accessories to the drug delivery device.

The second aspect of the invention also addresses the problems of enabling monitoring of patients behaviour regarding adherence to prescribed medical treatment by using an external accessory to a medical device, e.g. an insulin pen, enabling the accessory to monitor and e.g. log and e.g. even later communicate the use of the device to another device or/and to an inherent display. U.S. Pat. No. 7,133,329 discloses an add-on monitoring accessory (i.e. a cap) to be mounted on a medical device, e.g. an insulin delivery pen, and which by incorporating a switch detecting removal of the cap from the pen provides an indirectly means to monitor if the patient is in compliance with the intended use of the pen. Although removal of the cap from the main portion of the pen can only be used as a somewhat weak indication that the user has taken an injection, the lack of cap removal is a sure circumstantial evidence that the patient has not taken an injection with the specific device at the specific time.

Many people has though a habit of taking off and putting on caps on pens (just few millimetres) leading to lots of misinformation when these events are stored in a cap or pen system as indirectly information for insulin pen injections. A method to reduce this amount of misinformation is to introduce a pattern recognition routine which could sort between probable and non probable correlations between dismounting of the cap and injections, e.g. a method setting up a minimum time for an injection to take place, e.g. as described in U.S. Pat. No. 7,133,329 where a minimum defined time is required for the interpretation that an insulin injection is taken, e.g. the cap must be off for at least 6 seconds to be interpreted as an injection. Often the stored injection information in the cap shall be communicated to another device e.g. a data logger device and the same cap/insulin pen demounting/disassembling sensor switch is used to initiate the communication by discriminating between different times determined patterns of dismounting and mounting of the cap/insulin pen, e.g. if the cap is demounted for more than 1 second but less than 6 seconds this signalling a request for communication. Finally many erroneous injection recordings are the result of a cap not mounted correctly on the insulin pen or spuriously disassembled while carried by the user or patient e.g. in a pocket, but in most of these events the cap is still loosely mounted on the insulin pen but not in its locked position. Thus, a more reliable correlation between injection and cap/insulin pen dismounting/mounting is desirable.

Correspondingly, a further embodiment of the invention introduces a second cap sensing switch, whereby two different cap-related events can be detected. More specifically, the below-described cap device is provided with first contact means operatable between a first condition and a second condition, the first condition indicating that the cap device is in a fully mounted position on the drug delivery device, the second condition indicating that cap device has been moved a first distance away from the fully mounted position, as well as second contact means operatable between a first condition and a second condition, the first condition indicating that the cap device is in a fully mounted position on the drug delivery device, the second condition indicating that cap device has been moved a second distance away from the fully mounted position, the second distance being longer than the first distance. The cap is further provided with control means adapted to detect an event pattern for when the first and second contact means have been operated between their respective first and second condition such that the control means can perform a pre-defined action if a given event pattern is detected.

For example, the second condition of the second contact means may be indicative of the cap being moved fully away from the drug delivery, and the second condition of the first contact means may be indicative of the cap being moved less than fully away from the drug delivery, e.g. by incorporating a first "axial detection" switch as well as a second "radial detection" switch (see below). The first switch is an axial operating switch sitting in the cap in a way where it can detect an axial movement of the cap away from the insulin pen. The second switch is a radial operating switch sitting in the cap in a way where it can detect a radial movement or rather a radial clearance of a spring loaded part of the switch detection system caused by the removal of the cap from the pen part covering the insulin cartridge. Hereby the second switch can be used for input for an algorithm determining the probable correlation between an injection and the removal of the cap in a much more reliable way than solely an axial first switch can. The algorithm can still use dismounted/mounted time information to further strengthen the correlation. The first switch can be used together with the second switch to signal if communication has to take place to another device. Also here the algorithm can be strengthened by time information.

In the following a number of exemplary decision patterns will be described.

Switch 1 on (cap and insulin pen completely assembled) AND

Switch 2 on (cap completely or loosely assembled)→

No communication and no injection

Switch 1 off (cap and insulin pen not completely assembled) AND

Switch 2 on (cap completely or loosely assembled)→

No injection

If the above switch information is combined with timing information, i.e. for how long is the assembling or/and disassembling taking place, it can be used for starting communication frame or not, e.g. condition valid for >3 seconds can be interpreted as a request for communication. Cap must be remounted/assembled to start a new request for communication if conditions again is obtained, e.g. >3 seconds.

Switch 1 off (cap and insulin pen not completely assembled) AND

Switch 2 off (cap completely disassembled from insulin pen

If the above switch information is combined with timing information, i.e. for how long is the assembling or/and disassembling taking place it can be used for discrimination between probable or not probable correlations between cap dismounted and injection, e.g. condition valid for >6 seconds Switch 1 on Switch 2 off Is a non-valid situation and will indicate a failure situation To further strengthen reliability an additional algorithm could detect if the dismounting has taken place for more than a given time indicating that the user has forgotten to mount the cap again on the insulin pen making the time period uncertain regarding injections taken or not.

Instead of using both a first axial switch and a second radial switch a single radial switch instead of a single axial switch will also result in much higher confidence level of the correlation between cap off and injection taken than the single axial switch solution. Also in such a single radial switch solution a discrimination between different times determined patterns of disassembling and assembling the cap/insulin pen can further increase the above mentioned confidence level.

The radial or/and axial switch could besides electromechanical alternatively or complementary be optical, magnetic, capacitive, inductive, electromagnetic, sound or based on other fields or mechanisms.

Most caps on insulin pens have a locked position when the cap is completely assembled with the insulin pen carried out by one or more taps on the insulin pen (or cap) and one or more corresponding recesses in the cap (or insulin pen) firmly locking and keeping the cap in completely assembled position but still easy to pull off when needed by the user, i.e. the user will feel a tactile feedback and/or hear the unlocking when the cap is removed. When the position of the cap is used as an indication for an injection having taken place, it is, as described above, important to reduce the misinterpretation of an unintended disassembling of the cap from the insulin pen. By utilising the second radial switch as described above a further reduction in misinterpretation by spuriously cap disassembly from insulin pen while carried by the user e.g. in his pocket can be achieved with a second lock system in the cap/insulin pen needed to be unlocked before the cap can be completely dismounted/disassembled from the pen. It could use holes or/and grooves or/and protrusions in the pen cartridge cover part combined with counterparts (protrusions or/and holes or/and grooves) in the pen either producing a certain resistance to overcome or a proper lock function, e.g. including one or more rotational movement by the cap against the insulin pen to dismount/disassemble the cap completely. It could also just be a more simple increased friction between the cap and insulin pen to reduce the probability of the spurious disassembly if the first lock is opened.

Figure 8:
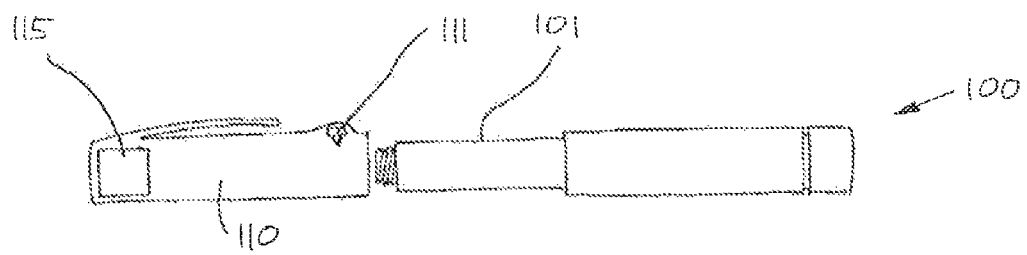
FIGS. 8 and 9 show a drug delivery pen with switches for detecting the position of a cap portion.

FIG. 8 shows an insulin pen assembly 100 comprising the pen per se 101 and a cap 110, the cap being adapted to detect full disassembling of the cap and the pen. The full disassembling cap switch 111 (a radial switch) is shown together with the electronic circuitry 115 to which switch output is delivered. The radial switch senses the presence or not of the insulin pen cartridge enclosure.

Figure 9:
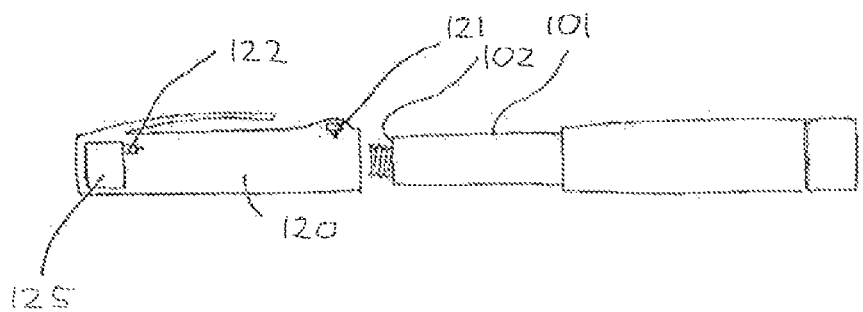

FIG. 9 shows an insulin pen assembly comprising the pen per se 101 and a cap 120, the cap being adapted to detect full disassembling of the cap and the pen and as well as partial disassembling. The full disassembling cap switch 121 (radial switch) and the partially disassembling cap switch 122 (axial switch) are shown together with the electronics 125 to which the switch outputs are delivered. The radial switch senses the presence or not of the insulin pen cartridge holder and the axial switch senses the presence or not of the distal end 102 of the insulin pen.

Figure 10:
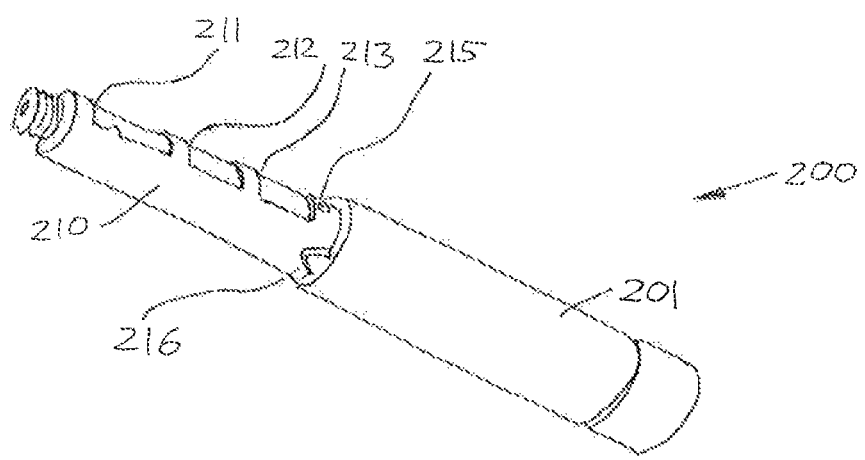
FIGS. 10-12 show a drug delivery pen and corresponding cap with means for controlling mounting and demounting of the cap on the pen.

FIG. 10 shows an embodiment provided with additional means to prevent unintentional removal of the cap from the pen. More specifically, the pen 201 comprises a cartridge holder 210 provided with first, second and third window bars 211, 212, 213 forming three windows, a lock tap 215 for a cap and a cap assembly guide 216. The not shown opposed side comprises corresponding structures.

Figure 11:
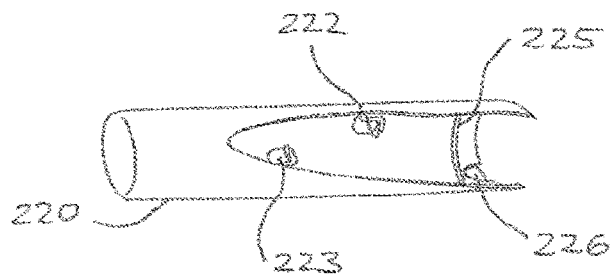

FIG. 11 shows a pen cap 220 with the counterpart 226 to the cap assembly guide 216, with a common recess lock 225 for the tap 215 and finally two rotational locks 222, 223 which will function together with the former shown window bars. Thus, when the cap is dismounted it will be stopped by the first (the right in FIG. 11) rotational lock hitting the first (the right in FIG. 10) window bar and it can only pass if the rotational lock is rotated relative to the window bar by rotating the cap about a quarter of a turn. Now the cap can be dismounted until the next lock (to the left) hits the next window bar (the middle in FIG. 10) and the cap can only be passed if the cap is rotated about a quarter of a turn again. Finally the first rotational lock hits the last window bar (the left in FIG. 10) and again only a quarter of a rotation of the cap can finally make the cap to be fully dismounted from the insulin pen.

Figure 12:
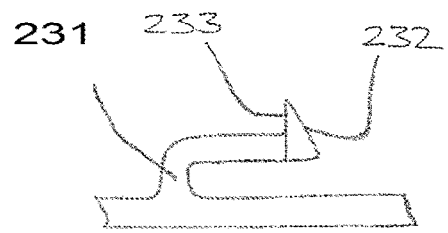

FIG. 12 shows an enlarged view of one of the two identical rotational locks. It is her exemplified by a snap lock with a cornered elastic part, an arm 231 and a head 232 with a sharp edge 233 and a rounded side. The two last edges (not shown) on the head part are also rounded. When the cap is mounted and assembled on the insulin pen the shown rounded side edges (see FIG. 11) will press the arm inside and allow the head and thereby the cap to pass when meeting a window bar. But the sharp edge will prevent the cap to be removed when hitting a window bar and must be rotated as described in the former drawing. In this way the risk of unintended removal of the cap is minimized.

The third aspect of the invention also addresses the problems of enabling monitoring of patients behaviour regarding adherence to prescribed medical treatment by using monitoring means to monitor and log and eventually later communicate the use of the device to another device or/and to an inherent display. Such a monitoring function may be build into both durable (i.e. re-fillable) medical devices (e.g. insulin pens) and disposable (i.e. pre-filled) medical devices but results often in a bulky appearance of the device. As described above, an add-on monitoring accessory may be mounted onto a medical device but also this would result in a bulky appearance. One of the major parts for providing the above functionality and key responsible for the resulting bulky appearance and also contributing to the cost is the necessary energy source, normally a primary battery (in the context of the present application the term "battery" also covers a single electric cell, e.g. a traditional 1.5 V cell).

Having regard to the above, embodiments in accordance with the third aspect of the present invention reduces the problem with bulky and expensive either add-on accessories or build in monitoring functionality in a medical device, e.g. a disposable pre-filled insulin pen, by providing the energy to drive all the functionality of the monitoring, displaying and/or communication means by another part where the space and sufficient durability and expense can be offered. More precisely, a primary battery can be contained in the inevitable insulin pen cap most insulin pens are supplied with. The cap is provided on common insulin pens for two main reasons: Primary for protecting the insulin against light radiation, especially from UV light and secondary protecting a mounted needle against mechanical damage (although recommended that the needle is renewed before each injection many users still reuse the needle). Further, the cap is a major part of the identity and design appearance of the insulin pen and will tend to make the pen discrete (in contrast to not having the cap on). It follows from the above reasons that insulin pen users always remount and keep the cap on the insulin pen after it has been removed during injection.

Thus, a battery (or other energy providing source) is placed in the insulin pen cap with means to transfer necessary energy to the insulin pen itself, either by galvanic connection or wirelessly. It follows, that such a cap could be (i) a durable part following the successively used disposable pens (reducing a bulky appearance of the pen and reducing the overall cost), (ii) a disposable part following the also disposable pen (reducing a bulky appearance of the pen), (iii) a durable part for a durable device (reducing a bulky appearance of the pen), or (iv) a disposable part for a durable device (where it provide a mean for shifting the battery and at the same time e.g. reducing a bulky appearance of the pen—by offering possible battery shift opportunity more functionality of the pen can be offered (requiring more electrical energy). In this way a number of advantages can be achieved, e.g. less bulky insulin pen, the option of more energy demanding functionality in the insulin pen, possibly lower overall cost of the insulin pen system, and a more elegant and discrete electronic insulin pen system.

The pen cap thus provides means for applying electrical energy to the insulin pen either galvanic during electrical contacts/connectors or wirelessly through a magnetic field by induction. In the insulin pen the energy is stored for later use by charging (recharging) a secondary battery or/and a capacitor. In a first embodiment with galvanic means, at least two connectors are provided between the cap and the insulin pen to establish a current path by which the secondary battery or/and capacitor is charged by the cap's electrical energy source (e.g. primary battery). In a second embodiment with wireless inductive means, an alternating current path is established in a first coil in the cap creating an alternating magnetic field in part of the insulin pen where a second coil surrounds part of the alternating magnetic field and generates an electric voltage by induction which is used to charge the secondary battery or/and capacitor.

If the pen cap provides galvanic energy transfer the primary battery voltage can be always on the connector terminals of the cap. The insulin pen draws current and power as needed. The connector terminals of the cap as well as the insulin pen must be protected against short-circuiting (e.g. one terminal on each part having a covered terminal (female part) and the opposite on each part having a non-covered terminal (male part). If the pen cap provides wireless inductive energy transfer the cap should only initiate the alternating magnetic field when needed. This could be achieved by measuring the impedance change coming from the presence of the secondary coil in the insulin pen when cap mounted or by a cap sensing switch (sensing the presence of the insulin pen) combined with a certain active time for the alternating field and a possible refreshing after a predetermined time. The cap and the insulin pen could also provide means to communicate by wireless means including magnetic fields e.g. utilising the present two coils in the cap respectively the insulin pen. And the pen requiring power as needed.

The electronic circuitry located in the pen, and provided with energy as described above, may be provided with a desired functionality. For example, the insulin pen may monitor and store injection related data. This could be data as injection time, injection amount, insulin type etc. or it could be cap on/cap off information. The last mentioned information can be achieved by the same galvanic connector means described above by measuring the voltage or the impedance in the cap or it could be by adding further connectors and detection means or by new specific cap detection means, e.g. a switch in the pen able to sense the presence of the cap on the insulin pen. It could also be by measuring an alternating magnetic field from the cap or the change in inductance caused by the presence of the primary coil in the cap (without the magnetic field—shut down) seen by the pen's coil.

It follows from the above description that the primary source for driving the electronic functionality in the pen comes from the electrical source in the cap. It also follows that the continuing of this functionality requires the presence of the cap with its energy source now and then. If this presence is missing too long the local energy resource in the insulin pen can be depleted. To let the pen be able to communicate such a state the following electronic system can be implemented: Either, letting the insulin pen's electronic system having means for detection a low power situation, meaning a detectable low threshold level of the secondary battery or/and capacitor voltage indicating the energy (voltage) in almost worn out, but still high enough for the electronic system to store this information in a reliable manner in a non-volatile memory location. This memory location is then read and communicated when the system is powered again and information is communicated. The power down electronic software routine could also store non-volatile the time the situation had occurred. Alternatively, having a certain non-volatile memory location pre-stored when the system is initialized with a value information saying that the system has been in above undesired state and having the system to always read this memory location when power is re-established in the electronic system in the pen for later communicating the information. A more harsh functionality could be a lock mechanism prohibiting the possibility of making injections if the electronic system is not powered properly forcing the user to mount (and remount) the cap to charge the insulin pen's secondary power source.

Figure 13:
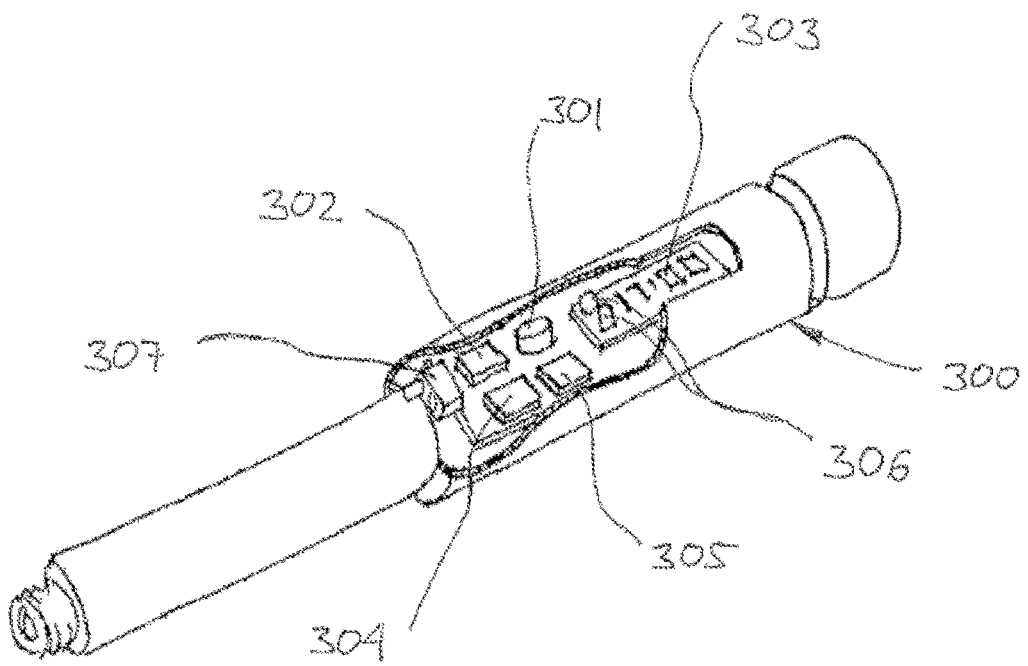
FIG. 13 shows a drug delivery pen with electronic circuitry.
Figure 14:
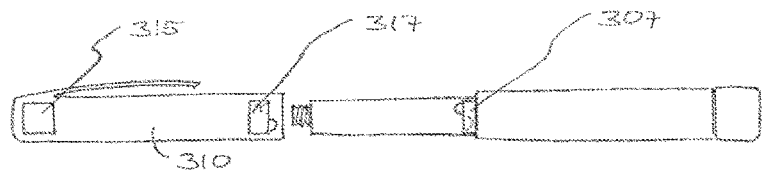
FIGS. 14 and 15 shows a drug delivery pen and corresponding cap adapted to electrically charge the pen.

In a first embodiment shown in FIG. 13 a drug delivery pen comprises a cap 310 (see FIG. 14) having a primary battery and galvanic connectors to an insulin pen. The pen 300 comprises a secondary battery 301, sensor means 302 for detecting movements from a drug expelling mechanism (not shown), a display 303, a micro-processor 304, non-volatile memory 305, a communication gate 306, e.g. IR transmitter and receiver, and a two pole connector 307. The two pole connector is adapted to connect to a corresponding power source counterpart connector in the cap (not shown). FIG. 14 shows the power connectors 307, 317, each having a male and female connector part. In the cap also the primary battery 315 is shown.

Figure 15:
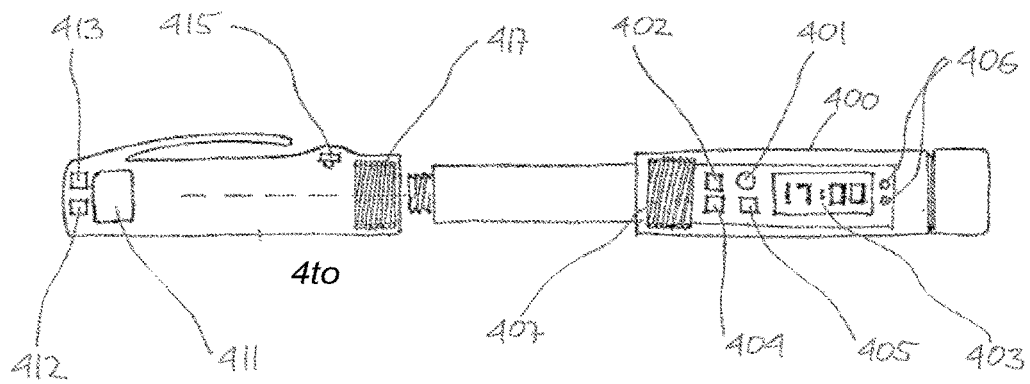

In a second embodiment shown in FIG. 15 a drug delivery pen assembly comprises a cap 410 having a battery 411, a micro-processor 412, a coil driving electronics circuit 413 and a coil 417 adapted to provide the pen counterpart coil 407 with an alternating magnetic field. Also shown is a radial switch 415 as described above. The pen part 400 comprises a pick-up coil 407, a secondary battery 401, sensor means 402 for detecting movements from a drug expelling mechanism (not shown), a display 403, a micro-processor 404, non-volatile memory 405, and a communication gate 406, e.g. IR transmitter and receiver.

Figure 16:
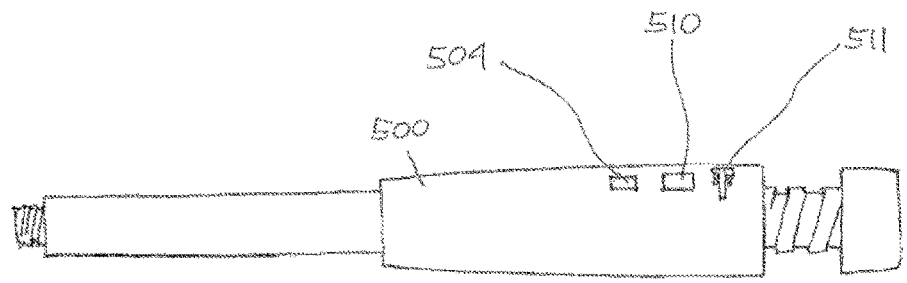
FIG. 16 shows a drug delivery pen with means controlling use of the pen.

The delivery pen 500 shown in FIG. 16 provides a pen lock mechanism prohibiting performing injections if the electronics system is not powered properly. The pen comprises a micro-processor 504 adapted to receive sensing output from a switch sensor 510 indicating that out-dosing of drug is to be performed (e.g. by sensing pressure on the dosing button), whereby the micro-processor activates an electromagnetic lock mechanism 511, this allowing the button to be actuated.

The fourth aspect of the invention also addresses the problems of enabling monitoring of patients behaviour regarding adherence to prescribed medical treatment by using monitoring means to monitor and log and eventually later communicate the use of the device to another device or/and to an inherent display, this allowing the collected information to be used by the patient and/or an attending health care professionals, e.g. the GP.

This monitoring of the patients taking of medicine will in many systems be acquired by the insulin pen itself (e.g. by the devices described above) and the information communicated to a data logger device at suitable moments for further upload to a data processing system. The data logger and the data processing can also be integrated in the same physical device or be even further separated into a first data logging system communicating to a second data logging system and the second data logging system (e.g. a PC) communicating to a data processing system (e.g. a remote server). When a patient uses several pens, e.g. one or more at the home and/or one or more at the work place, e.g. with different types of insulin, the patient will have the problem of bringing all the insulin pens to the data logger system or bringing the data logger system to the different pens. This inconvenience and the risk of loosing data will be even further enhanced when the data acquiring and storing is taking place in disposable medical devices (e.g. disposable insulin pens) not meant to be kept after use. Further, many diabetics also have several BGMs (Blood Glucose Meters) which may upload information to a data logger.

Having regard to the above, embodiments in accordance with the fourth aspect of the present invention provides an intermediate device adapted to communicate with and to store data from different medical devices for later communication with the data logger device.

The intermediate device could be another insulin pen, a cell phone, another medical device e.g. build into a BGM or a dedicated intermediate storing device. If the intermediate data storing device is another insulin pen it is able to communicate and store information from several insulin pens. It could either be exactly of the same type as the one it shall receive information from or it could be of another type but containing the same communication means including an agreed communication protocol. The information could also go both ways such as both pens contain the same information after the communication has taken place, hereby making it less probable that information is lost before communicated to the data logger system. If the intermediate data storing device is a different type of medical device than the first medical device, e.g. a BGM, then existing means on the second device can be used to extend the overall functionality of the first and second device. For example, the display on the BGM can be used to show a number of data sets from the first medical device, e.g. information of taken insulin, time, amount or type, in the same way as measured and stored BG data can be shown on most existing BGM in a display.

As most diabetics have more than one insulin pens diabetics also have more than one BGM meters. So the inter-device communication between insulin pens and insulin pens and between insulin pens and BGMs can also be extended to inter-device communication between different BGMs to increase flexibility and secure data from the many and different devices used by diabetics. It could be further extended to include heart pulse measuring, blood pressure measuring, food intake, exercise and/or other desirable data. A dedicated data communication and storing device could be a key-ring alike or credit card alike or other easy to wear shaped device. Also a common electronic device could be used, e.g. a cell phone with the necessary physical communication mean combined with a dedicated embedded program, e.g. in the form of a Java applet. In another embodiment the intermediate communication and data storing device could itself also contain the data logger. E.g. the dedicated communication and storing device or the cell phone (including e.g. the Java applet) could contain a communication gate to upload the stored data directly to the second data logger or to the data processing system. When a cell phone is also a data logger it could even be further elaborated to also contain all or part of the data processing system.

Figure 17:
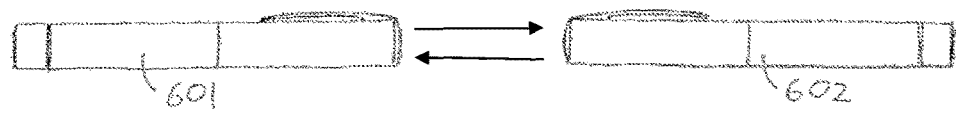
FIGS. 17-21 show systems in which medical devices are adapted to communicate with each other.
Figure 18:
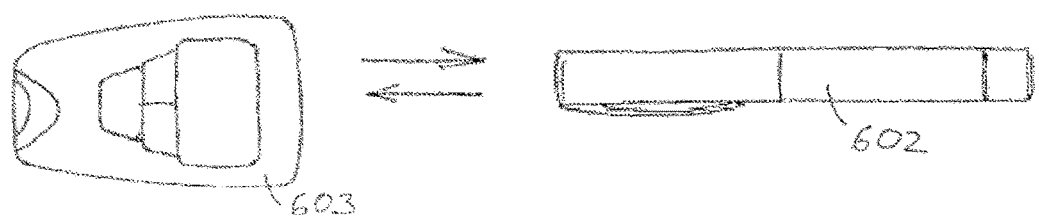
Figure 19:
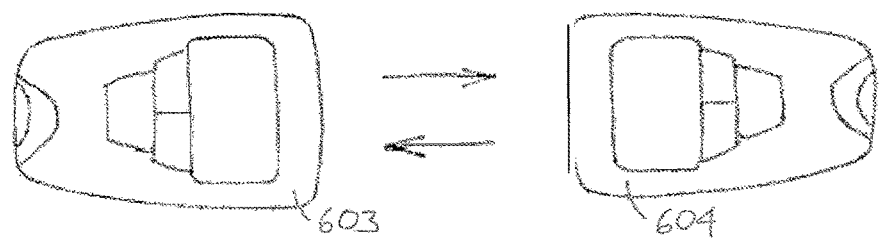

FIG. 17 shows a system comprising first and second medical devices in the form of two drug delivery pens 601, 602, each comprising electronic circuitry for generating data, a reservoir for a drug, an outlet for the drug, and a drug expelling mechanism for expelling drug from the reservoir and out through the outlet. One of the pens (i.e. the "higher ranking") serves as a data collecting device and comprises electronic circuitry for receiving, storing and transmitting data. The lower ranking pen is adapted to transmit data to the data collecting device (in form of the other pen), from which the received data can be collected and subsequently transmitted to an external device or system. Data may also be received from an external source. Transmission of data may take place by wireless means (e.g. IR, RF) and transmission of data may take place automatically when the data collecting device and a medical device are in the proximity of each other, e.g. within 10-20 cm. As IR is direction oriented automatic transmission is preferably based on RF communication. FIG. 18 shows a system comprising a pen 602 and a BGM 603 adapted to communicate with each other, and FIG. 19 shows a system comprising two BGMs 603, 604.

Figure 20:
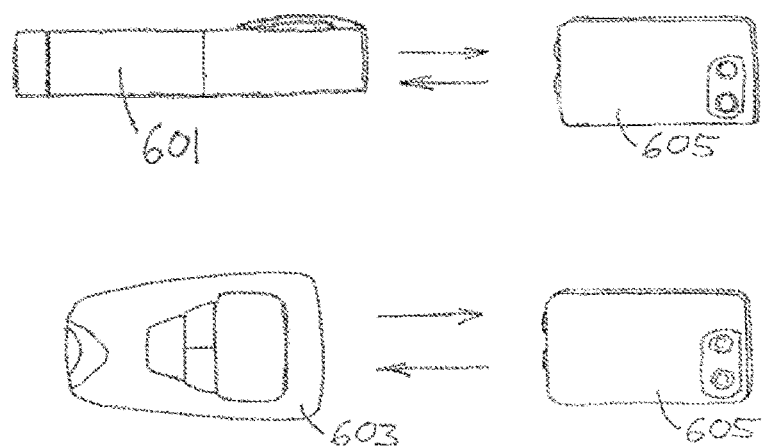
Figure 21:
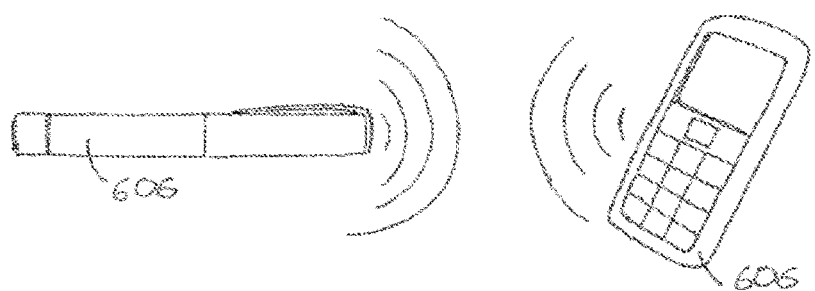

FIG. 20 shows a system comprising first and second medical devices in form of a pen-formed drug delivery device 601 and a BGM 603, as well as a data collecting device 605 in credit card form. Apart from being able to communicate with the data collecting device, the two medical devices may also be adapted to communicate with each other as described above. FIG. 21 shows a system in which the data collecting device is in the form of a cell phone 606. The communication may be by e.g. RF, IR or NFC (near field communication). The stored data can be displayed on the phone, e.g. by running an Applet on the phone whereby data can be stored, processed and displayed and also send to another device, e.g. another medical device, another phone, a server or the like.

As mentioned above, communication between devices may be by wireless means, e.g. be by IR. Correspondingly, a fifth aspect of the invention addresses issues related to enabling monitoring of patients behaviour regarding adherence to prescribed medical treatment electronics in a medical device or attached to a medical device to sense, achieve, log (store), display and communicate this information to another device. One problem to this capability is the amount of functionality against power & energy requirements especially within the frame of a battery powered wearable medical device and especially for durable devices (which shall last for several years). One of the major power and energy demanding functions is often seen to be the communication part. Therefore a way to reduce the overall power and energy requirements is to reduce the necessary power requirement for the communication part. In the following focus will be on the often used infrared communication (IR) but the disclosed concepts are not restricted to only this specific embodiment. Thus, in the following a number of different or rather complementary technical solutions to the problem are described:

Relevance of Data (Reducing the Amount of Data to be Sent)

If devices first communicates and agree on when data is to be send between them (one-way or bi-directionally) energy can be saved (instead of sending all information each time communication takes place only data from a certain date is sent). For example, a data logger (which may be a medical device itself) sends a request with information to a medical device when data is to be send, or data may be send from the device with an optional header telling from when data is sent (the date) and only data from this date is sent
Pre-processing of Data (Reducing the Amount of Data to be Sent)

The communication power (and energy) can be reduced by not sending raw data but processed data and/or compressed data. For example, data is analysed and only the output (resulting outcome) of this analyse is transmitted (fewer data), or data is compressed and the packed data (fewer data) sent for later unpacking in the receiving device. These methods can be applied simultaneously.
Adaptive Power Adjustment If the medical device and the data logger or other medical devices to be communicated with first agrees on the power level for the data communication between the two devices power can be saved in the medical device as well as the data logger (or other medical device). The agreement is based on the received level for one of the devices relative to the transmitted level for the other device, whereby the transmitting level and receiver amplification can be based on actual conditions, e.g. distance from each other, alignment, component performance, external and internal noise of the devices etc. and not the designable worst case (or just designable statistical acceptable) situation, this in order to minimize power as well as energy demand for the wanted communication. The transmitting level and receiver gain setup can further be based on a continuously agreement, e.g. one device communicates back to the other device at appropriate intervals during the communication the demand for communicated signal level (power) and vice versa.

For adaptive power adjustment for transmitter (and optionally also of the receiver gain) a scheme may be: The first device sends (communicates) with maximum level and the second device receives with maximum gain. The second device then sends data back to first device either telling it too which level it can reduce the transmitting level or sends back data by which the first device can calculate to which level it can reduce the transmitting level and still contain a reliable communication to the second device. The receiver adjusts optionally its receiving gain in accordance to the data information sent to the first device in order to establish the desired signal (power or level) and signal to noise performance. The first device then sends a data frame to the second device optionally containing transmission level information, e.g. in a header. The second device then sends acknowledge return data to the first device containing information either about the receiving level or information about wanted future transmitting level or data by which the first device can calculate the future transmitting level. The above transmitting/receiving information and adjustment continues during data communication. The described transmission/receiving adjustment can be for each sent frame or for clusters of the sent frames, just as the adaptive transmission/receiving adjustment can be one way between the two devices or both ways between the devices and it can be one way at a time or both ways simultaneously. The required (demanded) transmitting power level is based on received signal level and/or received signal/noise level and/or a safety factor taking into account rapid communication power signal and/or noise fluctuations. If communication is interrupted intentionally or unintentionally the high level high gain scheme is repeated.
Alignment Means to align optical components, e.g. LEDs, other light emitting components, phototransistors (photodiodes), lenses, etc., may be implemented in the devices in the production process or in the device design itself to make the optical communication path more accurate in regard to the expected light path route, i.e. alignment between expected and real optical path. Components that are part of a communication path often have obliquities or minor flaws which can be corrected by a physical adjustment of the devices and/or components. Components may be physically adjusted in the devices in order to align the physical communication path in accordance to the expected (conceived) communication path by measuring and adjusting. The communication path may alternatively be adjusted or aligned in order to align the physical communication path in accordance to the expected communication path by placing an intermediate transponder device in the communication path which can change the communication path in the device, e.g. an adjustable mirror or light guide if the communication signal is carried by light.
Optical Filtering and Amplifying Optical means may be used to reduce necessary power in optical data transmission in medical devices, e.g. if infrared communication (e.g. IRDA) is used. For example, optical band pass filters may be used in receivers to minimise noise signals in other frequencies than the narrow band IR signal chosen (e.g. by an IR LED). Lenses can be used to amplify light at the receivers and collect and narrow (amplifying) the light beam from the transmitters, e.g. IR laser LED. Both of these components could be merged into the same component, e.g. a lens only transferring and amplifying a band pass narrowed path of the spectrum of frequencies.
Different Wavelength (Frequencies) of the Transmitters and Receivers When constructing IR communication devices one problem is that the receiver can be sensitive to the devices' own transmitter. This is often noticeable when the receiver and transmitter are placed near each other or share an optical pathway, e.g. when receiving/transmitting through the same cover glass or hitting an external reflecting obstacle. A way to reduce this effect is to only send one way at the time (half duplex), although the effect of this can still reduce the independency of the receiver versus the transmitter because of possible charge build-up in the electrical amplifier/conditioner following the optical receiver component. A half duplex is also half as fast as a full duplex communication. One way to reduce this crosstalk is to use a transmitter and a receiver in each device sending on different frequencies. For example, a master device transmits on (optical) frequency 1 and receives on (optical) frequency 2, and the slave device receives on (optical) frequency 1 and transmits on (optical) frequency 2. Hereby master and slave devices can always separate their communication path. A single device could have communication means for both being a master and a slave, albeit one at a time, just as there may be more than one master and/or slave device.
IR Beam Guiding Indicator means may be used to reduce necessary power in optical data transmission. For example, a visible guide light may be used to show the user when the IR transmitter beam will 'hit' the receiver area if this is marked or definitely defined on the receiving device (the visible guide light is spatial super positioned with the IR light but is informatively adapted to the visual perception of the user). The visible guide light can be sent in a non-continuously matter, e.g. pulsating or mainly in the beginning of a communication. One or more indicators on the first medical device and/or the second medical device (e.g. data logger) may help the alignment for the optimal communication (e.g. sound, display) guiding the user in the placement of the two devices. For example, a display may show using a dot in a cross or an arrow and a dot how aligned the communication path is to the actual placement of the receiver component (or sensitive area) in the receiving device. These indicators can be based on the actual receiving and transmitting alignment and signal, and may be e.g. visual or mechanical guides helping the user to optimize his alignment of the two devices.

As appears, lowering overall power and energy consumption in a wearable medical device can be achieved utilizing one or more of the above-described concepts whereby the medical device can have more functionalities or last longer with the same battery or other power source or can have a smaller battery adding convenience to the device.

EXAMPLE 1

Relevance of Data (Reducing the Amount of Data to be Sent)

Two devices, e.g. a data logger and a medical device first communicate and agree on when data is to be sent from. The medical device prepares the sending of the requested data. The requested data is sent, eventually with a header defining (e.g. by date) the sent payload of data, and the data logger receives the data. The data logger processes the data.

EXAMPLE 2

Pre-processing of Data (Reducing the Amount of Data to be Sent)

Two devices, e.g. a data logger and a medical device optionally first communicate and agree on what data processing has to be performed before the data is sent. The medical device prepares the sending of the requested data. The requested processed data is sent, eventually with a header defining the processing, and the data logger receives the data. The data logger processes the data.

EXAMPLE 3

Adaptive Power Adjustment

A first device (e.g. medical device) sends with maximum transmission level and a second device (e.g. data logger) receives with maximum gain. The second device calculates the necessary transmission level and optionally the necessary receiver gain to achieve reliable communication. The second device returns data to the first device telling it to which level the transmitting level can be reduced and the receiver adjusts its receiving gain accordingly. The first device adjusts its transmission power to the needed level (requested by the second device) and sends a data frame to the second device. The second device sends an acknowledge data return to the first device containing information about wanted future transmitting level. The above transmitting/receiving information and adjustment continues during the data communication. If communication is interrupted unintentionally the high level high gain scheme may be repeated, initiated of the lack of acknowledge signal from second device.

EXAMPLE 4

Alignment

Means to align optical components in the devices in production process or in the device adapts to make the optical communication path more accurate in regard to the expected light path route (alignment between expected and real optical path). In such a process an optical component, e.g. an IR LED is arranged in a communication path of a medical device, e.g. in an insulin pen cap. The transmitting path from the LED itself is oblique and the transmitted IR light is therefore misaligned with the expected (conceived) communication path. To compensate for this the optical component is aligned (adjusted) in production so as the real communication path is aligned with the expected path by e.g. skewing the component assembly relative to the pen or by skewing of a fixture for the optical component in a similar manner. Instead of component alignment one or more intermediate refractive component(s) may be placed in the transmitting path with a refractive index fitted to align the communication path with the expected communication path. The refractive component may be a prism but any suitable optical component could be used. For both above methods only the alignment in one direction (dimension) is indicated to illustrate the principle but in a real device alignment solution two directions are necessary in order to secure the desired path, e.g. perpendicularly to the end edge of a pen cap.

EXAMPLE 5

Optical Filtering and Amplifying

A medical device, e.g. an insulin pen, is adapted to transmit a signal, e.g. IR light to a receiving device, e.g. a data logger. At the data logger an optical lens collects the beam from an area larger than the light receiving component in the data logger hereby amplifying the signal relative to the situation without the amplification lens. An optical band pass filter is also arranged in the transmission path allowing only frequencies similar to the transmitted signal to reach the receiver component almost un-attenuated but attenuating stray light hitting the optical receiver in the data logger with other frequencies than the signal, this providing a much better signal-to-noise ratio for a signal of a given strength from the transmitting device. The band pass filter could be interference filter, coated film, dichroic filter or other optical filters.

EXAMPLE 6

Different Wavelength (Frequencies) of the Transmitters and Receivers

A master device (e.g. a data logger) and a slave device (e.g. a medical device such as an insulin pen) communicate optically using in this example a LED and a photodiode for each device and a band pass filter in front of the photodiode in each device. The master device transmits on a certain frequency 1 using e.g. an IR LED with wavelength of about 850 nm. The master device has a receiver sensitive only to a different frequency 2, e.g. a photodiode with an optical band pass filter between 900 to 960 nm in the light path. The slave device receives on the frequency 1 using e.g. a photodiode with an optical band pass filter between 820 to 880 nm in the light path and transmits on frequency 2 using e.g. an IR LED with wavelength about 930 nm. The band pass filters could be interference filters, coated films, dichroic filter or other optical filters

EXAMPLE 7

IR Signal Beam Guiding

Superposition of a LED signal IR light and a visible LED guiding light, e.g. red light, can for example be performed by a partly transparent and partly reflective two sided mirror. The result is that a visible guiding light can show the user how (where) to align e.g. a medical device relative to a data logger, the visible light being super-positioned with the signal IR light and is the guiding light for the user when it is directed to the area on the receiving device where the IR light sensor is located. Alternatively, an assembly of the two light sources in one coincident assembly or almost coincident assembly with almost coincident light beams can be used.

In an alternative embodiment a medical device, e.g. an insulin pen, sends an optical signal to a receiving device, e.g. a data logger, the light coming from an IR LED in the pen cap. In the data logger a number of IR sensitive sensors, e.g. photodiodes, are used to receive the IR light and perform input for an algorithm calculating the alignment of the data logger and the medical device based on the relative received signal levels of the individual photodiodes. For example, the primary IR sensor may be encircled by 3 additional IR sensitive guiding sensors placed symmetrically around it. Alternatively both functions are combined such that the 3 guiding IR sensors are also used for receiving the communication signal from the medical device's IR light. Also angle misalignment where the two devices are not held perpendicular relative to each other can be calculated if the primary IR sensor is placed in an orifice whereby it will receive a lower signal than the other 3 surrounding sensors if the IR light is received above a certain angle from perpendicular. Also the distance and/or the necessary minimum distance between the data logger and the medical device can be calculated based on the absolute signal levels of the IR sensors. A display in the data logger shows the user how to move the data logger and/or medical device to perform optimum conditions for communicating between the medical device and the data logger.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

Listing of Examples

In the following different examples embodying the invention in accordance with the second aspect will be listed.

1. An assembly comprising:
(a) a drug delivery device comprising:
   a reservoir for a drug,
   an outlet for the drug,
   a drug expelling mechanism for expelling drug from the reservoir and out through the outlet,
and
(b) a cap device adapted to cover the outlet when mounted on the drug delivery device, the cap device comprising:
   first contact means operatable between a first condition and a second condition, the first condition indicating that the cap device is in a fully mounted position on the drug delivery device, the second condition indicating that cap device has been moved a first distance away from the fully mounted position,
   second contact means operatable between a first condition and a second condition, the first condition indicating that the cap device is in a fully mounted position on the drug delivery device, the second condition indicating that cap device has been moved a second distance away from the fully mounted position, the second distance being longer than the first distance, and
   control means adapted to detect an event pattern for when the first and second contact means have been operated between their respective first and second condition,
wherein
   the control means is adapted to perform an action if a given event pattern is detected.

2. An assembly as in example 1, wherein
   the second condition of the second contact means is indicative of the cap being moved fully away from the drug delivery, and
   the second condition of the first contact means is indicative of the cap being moved less than fully away from the drug delivery.

3. An assembly as in any of the previous examples, wherein
   the drug delivery device comprises an oblong portion defining an axial orientation and with the outlet being arranged at the distal end thereof,
   the cap device comprises a generally oblong cavity adapted to receive the oblong portion of the drug delivery device thereby covering and protecting the outlet, and
   the second condition of the second contact means is indicative of the cap device being moved away from the drug delivery device at least 50% of the way sufficient to allow the cap device to fully be moved perpendicularly away from the drug delivery device, this being indicative of the cap having been fully removed from the drug delivery device.

4. An assembly as in any of the previous examples, wherein the event pattern corresponds to the event that the second contact has been in its second condition in a predetermined amount of time, the corresponding action performed by the control means being the creation of a time log representing the detected event as a function of time.

5. An assembly as in any of the previous examples, wherein the event pattern corresponds to the event that the second contact has been in its first condition in a predetermined amount of time, and the first contact has been in its second condition in a predetermined amount of time, this being indicative of the cap not having been fully mounted on the drug delivery device, the corresponding action performed by the control means being the creation of a time log representing the detected event as a function of time.

6. An assembly as in any of the previous examples, wherein the cap device comprises means for transferring data to an external device, e.g. by wireless means.

7. An assembly as in any of the previous examples, wherein the reservoir is prefilled with a fluid drug.

8. An assembly comprising:
(a) a drug delivery device comprising:
   an oblong portion defining an axial orientation, and
   an outlet being arranged at the distal end of the oblong portion,
and
(b) a cap device adapted to cover the outlet when mounted on the drug delivery device, the cap device comprising:

a generally oblong cavity adapted to receive the oblong portion of the drug delivery device thereby covering and protecting the outlet, contact means operatable between a first condition and a second condition, the second condition being indicative of the cap device being moved away from the drug delivery sufficiently to allow the cap device to be moved perpendicularly away from the drug delivery device, this being indicative of the cap having been fully removed from the drug delivery device, and control means adapted to detect the event pattern for when the contact means have been operated between the first and second condition, wherein the control means is adapted to perform an action if a given event pattern is detected.

9. An assembly comprising:
(a) a drug delivery device comprising:
   a reservoir for a drug,
   an outlet for the drug,
   an oblong portion defining an axial orientation and with the outlet being arranged at the distal end thereof,
   a drug expelling mechanism for expelling drug from the reservoir and out through the outlet,
and
(b) a cap device adapted to cover the outlet when mounted on the drug delivery device, the cap device comprising:
   a generally oblong cavity adapted to receive the oblong portion of the drug delivery device thereby covering and protecting the outlet,
   contact means operatable between a first condition and a second condition, the first condition indicating that the cap device is in a fully mounted position on the drug delivery device, the second condition indicating that the cap device has been moved away from the drug delivery device at least 50% of the way sufficient to allow the cap device to fully be moved perpendicularly away from the drug delivery device, this being indicative of the cap having been fully removed from the drug delivery device.

In the following different examples embodying the invention in accordance with the third aspect will be listed.

1. An assembly comprising:
(a) a drug delivery device comprising:
   a reservoir for a drug,
   an outlet for the drug,
   a drug expelling mechanism for expelling drug from the reservoir and out through the outlet,
   electronic circuitry, and
   a secondary power source for storing energy for driving the electronic circuitry,
and
(b) a cap device adapted to cover the outlet when mounted on the drug delivery device, the cap device comprising:
   a primary power source adapted to provide energy to the secondary power source,
wherein
   the drug delivery device and the cap device are provided with interacting transfer means adapted to transfer energy from the primary power source to the secondary power source when the cap device is mounted on the drug delivery device.

2. An assembly as in example 1, wherein
   the cap device and the delivery device comprise interacting coupling means for releasably mounting the cap device on the delivery device in an storing position, and energy is transferred from the primary power source to the secondary power source when the cap device is mounted on the drug delivery device in its storing position.

3. An assembly as in any of the previous examples, wherein:
   energy is transferred from the first energy means to the secondary energy means using a means from the group consisting of the members: galvanic contact and wireless transmission,
   the primary power source is selected from the group consisting of the members: an electric battery, a rechargeable electric battery, an electric condensator, a user-operatable electric generator,
   the secondary power source is selected from the group consisting of the members: a rechargeable electric battery, an electric condensator.

4. An assembly as in any of the previous examples, wherein the electronic circuitry is adapted to perform one or more functions selected from the group consisting of the members:
   generating data representing the size of a dose set by the drug expelling mechanism,
   generating data representing the size of a dose expelled by the drug expelling mechanism,
   generating and storing a time log for data representing sizes of doses set by the drug expelling mechanism,
   generating and storing a time log for data representing sizes of doses expelled by the drug expelling mechanism,
   generating data representing the type of drug contained in the reservoir,
   transmitting data to an external receiver,
   receiving data from an external transmitter,
   controlling a display adapted to display user-readable information,
   controlling indication means adapted to indicate when the secondary power source need to be recharged,
   controlling control means adapted to prevent a dose to be set or expelled when the secondary power source need to be recharged.

5. An assembly as in any of the previous examples, wherein the reservoir is prefilled with a fluid drug.

In the following different examples embodying the invention in accordance with the fourth aspect will be listed.

1. A system comprising:
(a) at least first and second medical devices, each comprising:
   electronic circuitry for generating and transmitting data,
and
(b) a data collecting device comprising:
   electronic circuitry for receiving, storing and transmitting data,
wherein
   the medical devices are adapted to transmit data to the data collecting device, and
   the data collecting device is adapted to receive data from at least one medical device and transmit the received data to an external device or system.

2. A system as in example 1, wherein at least one of the medical devices is a drug delivery devices comprising:
   a reservoir for a drug,
   an outlet for the drug, and
   a drug expelling mechanism for expelling drug from the reservoir and out through the outlet.

3. A system as in example 1 or 2, wherein at least one of the medical devices is a BGM.

4. A system as in any of the previous examples, wherein the data collecting device is in the form of one of the medical devices.

5. A system as in any of the previous examples, wherein the data collecting device is in the form of one of the following devices:
 a BGM,
 a CGM,
 a drug delivery device,
 a mechanical drug delivery device,
 an electronically controlled drug delivery device,
 a PDA,
 a mobile phone,
 a key ring device.

6. A system as in any of the previous examples, wherein at least one medical device is in the form of one of the following devices:
 a BGM,
 a CGM,
 a drug delivery device,
 a mechanical drug delivery device,
 an electronically controlled drug delivery device.

7. A system as in any of the previous examples, wherein transmission of data between a medical device and the data collecting device takes place by wireless means.

8. A system as in example 7, wherein transmission of data takes place automatically when the data collecting device and a medical device are in the proximity of each other.

9. A system as in any of the previous examples, wherein at least one medical device comprises a reservoir prefilled with a fluid drug.

10. A system as in any of the previous examples, wherein the data collecting device is adapted to transmit the received data to an external device or system.

11. A system comprising:
(a) at least first and second drug delivery devices, each comprising:
 a reservoir for a drug,
 an outlet for the drug,
 a drug expelling mechanism for expelling drug from the reservoir and out through the outlet, and
 electronic circuitry for generating and transmitting data, and
(b) a data collecting device comprising:
 electronic circuitry for receiving, storing and transmitting data,
wherein
 the drug delivery devices are adapted to transmit data to the data collecting device,
and
 the data collecting device is adapted to receive data from at least one drug delivery device and transmit the received data to an external device or system.

The invention claimed is:

1. A monitoring device adapted to be mounted on a drug delivery device,
 the drug delivery device, when present, comprising:
  a reservoir for a drug,
  an outlet for the drug,
  a drug expelling mechanism for expelling the drug from the reservoir and out through the outlet,
  a housing in which at least a portion of the drug expelling mechanism is arranged, and
  a first coupling structure for a cap,
  the cap adapted to cover the outlet and comprising:
   a second coupling structure for engaging the first coupling structure,
 the monitoring device comprising:
  a housing portion,
  a structure for detecting or registering an action performed in the drug delivery device, and
  a third coupling structure adapted to engage the first coupling structure on the drug delivery device,
  whereby the monitoring device when mounted to the drug delivery device is arranged in a pre-determined position relative to the drug delivery device when the first and third coupling structure engage each other, thus allowing information to be transferred between the drug delivery device and the monitoring device, and
  whereby the monitoring device does not cover the outlet when arranged in the mounted position, thus allowing an amount of drug to be expelled from the reservoir while the monitoring device is coupled to the drug delivery device.

2. The device as in claim 1, wherein the monitoring device comprises a fourth coupling structure adapted to engage the second coupling structure, thus allowing the cap to be attached to the drug delivery device via the monitoring device.

3. The device as in claim 1, wherein the monitoring device comprises a fourth coupling structure adapted to engage fifth coupling structure arranged on a second cap (40), thus allowing the second cap to be attached to the drug delivery device via the monitoring device.

4. The device as in claim 1, wherein the monitoring device comprises a structure (36, 37, 38, 39) for biasing a portion of the monitoring device against a housing portion of the drug delivery device to thereby enhance transfer of information between the two devices.

5. The device as in claim 1, wherein the monitoring device comprises a mounting portion (50, 750, 950) and a monitoring portion (60, 760, 960), the mounting portion comprising the third coupling structure (32 or 52), wherein the monitoring portion can be releasable from the mounting portion.

6. The device as in claim 5, wherein the mounting portion comprises a non-releasable coupling structure (58) for engaging the drug delivery device.

7. The device as in claim 1, wherein the monitoring device comprises a further coupling structure (33 or 53) adapted to engage a further specific coupling structure (10) on the drug delivery device.

8. The device as in claim 1, wherein the drug expelling mechanism comprises a mechanical structure and the structure for detecting is adapted to detect audible, optical, vibration or electromagnetic signals generated by the drug expelling mechanism.

9. The device as in claim 8, wherein the drug expelling mechanism is adapted to set and expel the set dose, the structure for detecting being adapted to detect the size of a dose being set and/or the size of a dose being expelled.

10. The device as in claim 1, wherein the monitoring device comprises structure for transferring data to an external device.

11. The device as in claim 10, wherein said structure for transferring data is a wireless structure.

12. The device as in claim 1, wherein the reservoir is prefilled with a fluid drug.

13. The device as in claim 1, wherein information is transferred through a housing portion of the drug delivery device by a non-galvanic structure.

14. The device as in claim 1, wherein the monitoring device can be arranged in a non-rotational mounted position relative to the drug delivery device.

15. The device as in claim 1, wherein the reservoir comprises a transparent area allowing a user to inspect at least a portion of the reservoir, and wherein the cap in its mounted position is adapted to cover the transparent area to thereby protect drug contained in the reservoir from ambient light.

* * * * *